United States Patent [19]
Myers et al.

[11] Patent Number: 5,618,265
[45] Date of Patent: *Apr. 8, 1997

[54] IONTOPHORETIC DELIVERY DEVICE WITH SINGLE LAMINA ELECTRODE

[75] Inventors: Robert M. Myers, Stanford; Felix A. Landrau, San Jose, both of Calif.

[73] Assignee: ALZA Corporation, Palo Alto, Calif.

[*] Notice: The term of this patent shall not extend beyond the expiration date of Pat. No. 5,543,098.

[21] Appl. No.: 592,083

[22] Filed: Jan. 26, 1996

Related U.S. Application Data

[63] Continuation of Ser. No. 197,665, Feb. 17, 1994, Pat. No. 5,543,098, which is a continuation of Ser. No. 667,714, Mar. 11, 1991, abandoned.

[51] Int. Cl.⁶ ........................................................ A61N 1/30
[52] U.S. Cl. ................................................ 604/20; 607/115
[58] Field of Search ................................... 604/20, 890.1; 607/149, 152, 115; 264/104–105, 126, 160; 424/422–438, 447–449

[56] References Cited

U.S. PATENT DOCUMENTS

| | | |
|---|---|---|
| 3,991,755 | 11/1976 | Vernon et al. . |
| 4,141,359 | 2/1979 | Jacobsen et al. . |
| 4,250,878 | 2/1981 | Jacobsen et al. . |
| 4,336,217 | 6/1982 | Saur .......................................... 264/105 |
| 4,367,745 | 1/1983 | Welage . |
| 4,383,529 | 5/1983 | Webster . |
| 4,398,545 | 8/1983 | Wilson . |
| 4,474,570 | 10/1984 | Ariura et al. . |
| 4,640,689 | 2/1987 | Sibalis . |
| 4,702,732 | 10/1987 | Powers et al. ............................. 604/20 |
| 4,731,049 | 3/1988 | Parsi ......................................... 604/20 |
| 4,744,787 | 5/1988 | Phipps et al. . |
| 4,747,819 | 5/1988 | Phipps et al. . |
| 4,752,285 | 8/1988 | Petelenz ................................... 604/20 |
| 4,764,164 | 8/1988 | Sasaki ...................................... 604/20 |
| 4,904,247 | 2/1990 | Therriault et al. ....................... 604/304 |
| 4,921,475 | 5/1990 | Sibalis ..................................... 604/20 |
| 4,957,593 | 9/1990 | Shaw et al. .............................. 204/291 |
| 5,032,109 | 7/1991 | Sibalis ..................................... 604/20 |
| 5,084,006 | 1/1992 | Lew et al. ................................. 604/20 |
| 5,087,240 | 2/1992 | Sibalis ..................................... 604/20 |
| 5,147,297 | 9/1992 | Myers et al. ............................. 604/20 |

FOREIGN PATENT DOCUMENTS

| | | |
|---|---|---|
| 0252732 | 1/1988 | European Pat. Off. . |
| 410009 | 5/1934 | United Kingdom . |

OTHER PUBLICATIONS

Dorland's Pocket Medical Dictionary, 23 Editon, p. 362.
CRC Handbook of Chemistry and Physics pp. D 151–158 67th Edition (1986–1987).
CRC Handbook of Chemistry and Physics pp. D–141 to D–146.

*Primary Examiner*—Mark Bockelman
*Attorney, Agent, or Firm*—Felissa H. Cagan; D. Byron Miller; Steven F. Stone

[57] ABSTRACT

An electrically powered transdermal iontophoretic delivery device (10, 20) and a method of making same is provided. The device utilizes electrode assemblies (8, 9) composed of a substantially homogenous blend of a polymeric matrix containing about 5 to 50 vol % of a conductive filler which forms a conductive network through the matrix, and up to about 50 vol % of the agent to be iontophoretically delivered through the skin. In the case of the donor electrode assembly, the agent is typically a drug and preferably a water soluble drug salt. In the case of the counter electrode assembly, the agent is typically an electrolyte salt. The homogenous blend eliminates the need for separate electrode and agent containing layers which require lamination.

19 Claims, 2 Drawing Sheets

IONTOPHORETIC DELIVERY DEVICE WITH SINGLE LAMINA ELECTRODE

This application is a continuation Ser. No. 08/197,655, filed Feb. 17, 1994, now U.S. Pat. No. 5,543,698 which is a continuation of Ser. No. 667,714 filed Mar. 11, 1991, now abandoned, and benefit of the filling date of said earlier filed application is claimed under 35 U.S.C. §120.

TECHNICAL FIELD

This invention relates to a device for delivering an agent transdermally or transmucosally by iontophoresis. More particularly, this invention relates to an electrically powered iontophoretic delivery device having a polymer-based electrode assembly and a method of making same.

BACKGROUND ART

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, U.S. Pat. No. 3,991,755 issued to Vernon et al; U.S. Pat. No. 4,141,359 issued to Jacobsen et al; U.S. Pat. No. 4,398,545 issued to Wilson; and U.S. Pat. No. 4,250,878 issued to Jacobsen disclose examples of iontophoretic devices and some applications thereof. The iontophoresis process has been found to be useful in the transdermal administration of meicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat, production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter indifferent, inactive or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Electroosmosis is the transdermal flux of liquid solvent (e.g., the liquid solvent containing the uncharged drug or agent ) which is induced by the presence of an electric field imposed across the skin by the donor electrode. As used herein, the terms "iontophoresis" and "iontophoretic" refer to (1) the delivery of charged drugs or agents by electromigration, (2) the delivery of uncharged drugs or agents by the process of electric osmosis, (3) the delivery of charged drugs or agents by the combined processes of electromigration and electroosmosis, and/or (4) the delivery of a mixture of charged and uncharged drugs or agents by the combined processes of electromigration and electroosmosis.

Furthermore, existing iontophoresis devices generally require a reservoir or source of, the beneficial agent (which is preferably an ionized or ionizable agent or a precursor of such agent) to be iontophoretically delivered into the body. Examples of such reservoirs or sources of ionized or ionizable agents include a pouch as described in the previously mentioned Jacobsen U.S. Pat. No. 4,250,878, or a preformed gel body as described in Webster U.S. Patent No. 4,383,529 and Ariura et al. U.S. Pat. No. 4,474,570. Such drug reservoirs are electrically connected to the anode or the cathode of an iontophoresis device to provide a fixed or renewable source of one or more desired agents.

More recently, iontophoretic delivery devices have been developed in which the donor and counter electrode assemblies have a "multi-laminate" construction. In these devices, the donor and counter electrode assemblies are formed of multiple layers of (usually) polymeric matrices, for example, Parsi U.S. Pat. No. 4,731,049 discloses a donor electrode assembly having hydrophilic polymer based electrolyte reservoir and drug reservoir layers, a skin-contacting hydrogel layer, and optionally one or more semipermeable membrane layers. Sibalis U.S. Pat. No. 4,640,689 discloses in FIG. 6 an iontophoretic delivery device having a donor electrode assembly comprised of a donor electrode (204), a first drug reservoir (202), a semipermeable membrane layer (200), a second drug reservoir (206), and a microporous skin-contacting membrane (22'). The electrode layer can be formed of a carbonized plastic, metal foil or other conductive films such as a metallized mylar film. In addition, Ariura et al, U.S. Pat. No. 4,474,570 discloses a device wherein the electrode assemblies include a conductive resin film electrode layer, a hydrophilic gel reservoir layer, a current distribution and conducting layer and an insulating backing layer. Ariura et al disclose several different types of electrode layers including an aluminum foil electrode, a carbon fiber non-woven fabric electrode and a carbon-containing rubber film electrode.

Transdermal iontophoretic delivery devices having electrodes composed of electrochemically inert materials, as well as devices having electrodes composed of electrochemically reactive materials are known. Examples of electrochemically inert electrode materials include platinum, carbon, gold and stainless steel. The prior art has also recognized that the electrochemically reactive electrode materials are in many cases preferred from the standpoint of drug delivery efficiency and pH stability. For example, U.S. Pat. Nos. 4,744,787; 4,747,819 and 4,752,285 all disclose iontophoretic electrodes composed of materials which are either oxidized or reduced during operation of the device. Particularly preferred electrode materials include silver as the anodic electrode, and silver chloride as the cathodic electrode.

Others have suggested using biomedical electrodes having current distribution members composed of a rubber or other polymer matrix loaded with a conductive filler such as powdered metal. See for example, U.S. Pat. No. 4,367,745. Such films however, have several disadvantages. First, as the metal particle loading in a polymer matrix approaches about 65 vol %, the matrix begins to break down and becomes too brittle to be handled. Even at metal particle loadings only about 50 to 60 vol %, the films produced are extremely rigid and do not confirm well to non-planar surfaces. This is a particular disadvantage when designing an electrode adapted to be worn on the skin or a mucosal membrane. An iontophoretic electrode adapted to be worn on a body surface must have sufficient flexibility to Contour itself to the natural shape of the body surface to which it is applied.

The drug and electrolyte reservoir layers of iontophoretic delivery devices have been formed of hydrophilic polymers. See for example, Ariura et al, U.S. Pat. No. 4,474,570; Webster U.S. Pat. No. 4,383,529 and Sasaki U.S. Pat. No. 4,764,164. There are several reasons for using hydrophilic polymers. First, water is the preferred solvent for ionizing many drug salts. Secondly, hydrophilic polymer components i.e., the drug reservoir in the donor electrode and the electrolyte reservoir in the counter electrode) can be hydrated while attached to the body by absorbing water from the skin (i.e., through transepidermal water loss or sweat) or from a mucosal membrane (e.g., by absorbing saliva in the case of oral mucosal membranes). Once hydrated, the device begins to deliver ionized agent to the body. This enables the drug reservoir to be manufactured in a dry state, giving the device a longer shelf life.

Hydrogels have been particularly favored for use as the drug reservoir matrix and electrolyte reservoir matrix in iontophoretic delivery devices, in part due to their high equilibrium water content and their ability to quickly absorb water. In addition, hydrogels tend to have good biocompatibility with the skin and with mucosal membranes. In spite of these advantages however, hydrogels and other hydrophilic polymer components are difficult to laminate to other components of the delivery system. For example, when utilizing a drug reservoir matrix or an electrolyte reservoir matrix composed of a hydrophilic polymer, the matrix begins to swell as it absorbs water from the skin. In the case of hydrogels, the swelling is quite pronounced. Typically, the drug or electrolyte reservoir is in either direct contact, or contact through a thin layer of an electrically conductive adhesive, with an electrode. Typically, the electrode is composed of metal (e.g., a metal foil or a thin layer of metal deposited on a backing layer) or a hydrophobic polymer containing a conductive filler (e.g., a hydrophobic polymer loaded with carbon fibers and/or metal particles). The electrodes (i.e., either metal electrodes or hydrophobic polymers containing a conductive filler), on the other hand, do not absorb water and tend not to swell. The different swelling properties of the hydrophilic reservoirs and the electrodes results in separation along their contact surfaces. In severe cases, this separation can result in the complete loss of electrical contact between the electrode layer and the reservoir layer resulting in an inoperable device.

In general, the greater the number of layers in a multi-laminate type electrode assembly, the greater is the likelihood of a system failure due to loss of electrical contact between adjacent electrode assembly layers. Furthermore, the greater the number of electrode assembly layers, the more complicated the assembling/manufacturing process wherein each of the individual layers must be consecutively laminated, one onto the next.

DISCLOSURE OF THE INVENTION

It is an object of this invention to provide an improved electrode assembly for an iontophoretic delivery device.

It is another object of this invention to provide an electrode assembly having fewer individual layers or laminae, and therefore having a reduced likelihood of electrical failure between adjacent layers.

It is a further object of this invention to provide a method of making an improved electrode assembly for an iontophoretic delivery device.

These and other objects are met by an electrically powered iontophoretic delivery device including a donor electrode assembly, a counter electrode assembly and a source of electrical power adapted to be electrically connected to the donor and counter electrode assemblies. The donor and counter electrode assemblies are adapted to be placed in agent transmitting relation with a body surface. At least One of the donor and counter electrode assemblies comprises a substantially homogenous blend of a polymeric matrix containing about 5 to 50 vol % of a conductive filler which forms a conductive network through the matrix, and from about 1 to 50 vol % of an agent to be iontophoretically delivered through the body surface.

Preferably, the polymeric matrix contains about 15 to 30 vol % conductive filler and about 10 to 50 vol % of the agent. Most preferably, the polymeric matrix contains about 20 to 25 vol % of the conductive filler and about 20 to 35 vol % of the agent. In the case of the donor electrode assembly, the agent is most preferably a drug or other therapeutic agent. In the case of the counter electrode assembly, the agent is most preferably an electrolyte salt.

Also provided is a method of making an electrode assembly for an electrically powered iontophoretic delivery device. The method comprises the steps of homogenously blending about 5 to 50 vol % of a conductive filler, and from about 1 to about 50 vol % of an agent to be iontophoretically delivered, into a polymeric matrix until the filler forms an electrically conductive network through the polymer matrix. The method further includes the step of forming the agent-containing blended mixture into a sheet. Preferably, the blending and sheet forming steps are performed in a rubber mill. Optionally, the sheet so obtained is calendered to a uniform desired final thickness.

MODES FOR CARRYING OUT THE INVENTION

Figure 1:
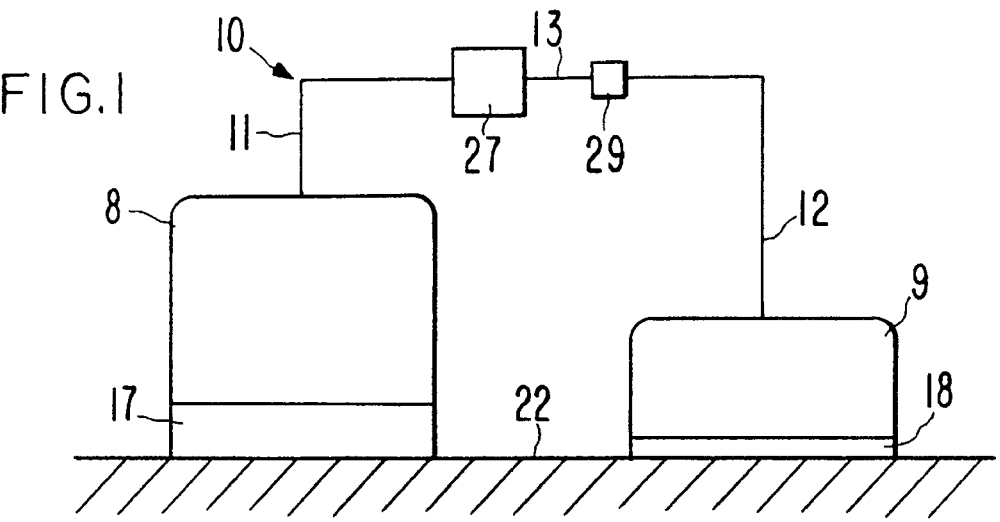
FIG. 1 is a schematic view of an iontophoretic drug delivery device according to the present invention.

FIG. 1 is a schematic view of an iontophoretic delivery device 10 for delivering a beneficial agent through a body surface 22. Body surface 22 is typically intact skin or a mucosal membrane. Iontophoretic delivery device 10 includes a donor electrode assembly 8, a counter electrode assembly 9, an electrical power source 27 (e.g., a battery) and an optional control circuit 19.

The donor electrode assembly 8 contains the beneficial agent (e.g., a drug) to be iontophoretically delivered by device 10.

The donor electrode assembly 8 is shown adhered to the body surface 22 by means of an ion-conducting adhesive layer 17.

Iontophoretic delivery device 10 includes a counter electrode assembly 9 which is placed on the body surface 22 at a location spaced apart from electrode assembly 8. Counter electrode assembly 9 is shown adhered to the body surface 22 by means of an ion-conducting adhesive layer 18. The donor and counter electrode assemblies 8 and 9 normally include a strippable release liner, not shown, which is removed prior to application of electrode assemblies 8 and 9 to body surface 22. Counter electrode assembly 9 contains a pharmacologically acceptable electrolyte salt. Suitable electrolytes for electrode assembly 9 include sodium chloride, alkaline salts, chlorides, sulfates, nitrates, carbonates, phosphates, and organic salts such as ascorbates, citrates, acetates and mixtures thereof. Electrode assembly 9 may also contain a buffering agent. Sodium chloride is a suitable electrolyte when the counter electrode assembly 9 is the cathode and is composed of silver/silver chloride, optionally with a sodium phosphate buffer.

When the device 10 is in Storage, no current flows because the device forms an open circuit. When the device 10 is placed on the skin or mucosal membrane of a patient, and the electrode assemblies 8 and 9 become sufficiently hydrated to allow movement of ions therethrough, the circuit between the electrodes is closed and the power source begins to deliver current through the device and through the body of the patient. Electrical current flowing through the conductive members 11,12 and 13 of the device 10 (i.e., those portions used to connect the power source 27 to the electrode assemblies 8 and 9) is carried by electrons (electronic conduction), while current flowing through the hydrated portions of the device 10 (e.g., the donor electrode assembly 8, the counter electrode assembly 9 and the ion-conducting adhesive layers 17 and 18) is carried by ions (ionic conduction). In order for current to flow through the device, it is necessary for electrical charge to be transferred from current carrying members 11 and 12 to chemical species in solution in electrode assemblies 8 and 9, respectively, by means of oxidation and reduction charge transfer reactions. The type of charge transfer reaction occurring within electrode assembly 8 or 9 will depend in part upon the polarity of the electrode assembly as well as the composition of the conductive filler added to the electrode assembly, as will be discussed in more detail hereinafter.

Electrode assemblies 8 and 9 are each comprised of a polymeric matrix containing a conductive filler and an agent (e.g., a drug or an electrolyte) to be iontophoretically delivered during operation of the device. Any polymer which can be suitably mixed with the conductive filler and the agent may be used as the polymeric matrix of electrode assemblies 8 and 9. Both hydrophilic and hydrophobic polymers can be used as the matrix of electrode assemblies 8 and 9. In addition, mixtures of hydrophilic and hydrophobic polymers may also be used. Examples of suitable polymers for use as the matrix of electrode assemblies 8 and 9 include, without limitation, polyalkenes, polyisoprenes, rubbers, polyvinylacetate, ethylene vinyl acetate copolymers, polyamides, polyurethanes, polyvinylchloride, polyvinyl pyrrolidones, cellulosic polymers, polyethylene oxides, polyacrylic acid polymers and mixtures thereof. A preferred polymeric matrix for electrode assemblies 8 and 9 is a mixture of: (1) a copolymer of ethylene vinyl acetate and (2) polyvinyl pyrrolidone.

The polymeric matrix of electrode assemblies 8 and 9 should contain about 5 to 50 vol %, preferably about 15 to 30 vol %, and most preferably about 20 to 25 vol % of a conductive filler which forms a conductive network through the polymeric matrix. The conductive filler forming the conductive network in the polymeric matrix may be comprised of either an electrochemically inert conductive material, an electrochemically reactive conductive material or a mixture thereof. As mentioned above, as electrical current flows through device 10 oxidation of some chemical species takes place within one of the electrode assemblies 8 and 9, while reduction of some chemical species takes place within the other electrode assembly. In cases where the conductive filler is comprised entirely of an electrochemically inert material which is unable to undergo oxidation or reduction during operation of the device, the water used to hydrate electrode assemblies 8 and 9 will be electrolyzed during operation of device 10. Unfortunately, the electrolysis of water results in the production of protons at the anodic electrode assembly and hydroxyl ions at the cathodic electrode assembly; In addition, gaseous hydrogen and oxygen are involved at the cathodic and anodic electrode assemblies, respectively. Since the electrolysis of water produces protons and hydroxyl ions, it is important to provide either appropriate buffers or to utilize an appropriate form of a drug, i.e., either an acid or base type drug when using exclusively electrochemically inert conductive fillers. For example, when the agent to be delivered i s a base (e.g., lidocaine, nicotine, etc.) the production of protons within the anodic donor electrode assembly 8 will act to convert the base to an ionizable (e.g., salt) form Which can be delivered from the device by electromigration. Similarly, when the agent to be delivered is an acid (e.g., cromolyn) the production of hydroxyl ions within the cathodic donor electrode assembly 8 will act to convert the acid to an ionizable (e.g., salt) form which can likewise be delivered from the device by electromigration.

Alternatively, and in many cases preferably, the conductive filler will be comprised, at least in part, of a material which is electrochemically reactive and participates in a charge transferring chemical reaction. Examples of preferred electrochemically reactive conductive fillers include silver, zinc, copper and silver chloride. The preferred oxidation/reduction reactions for these materials are shown below:

$$Ag \leftrightarrows Ag^+ + e^-$$

$$Zn \leftrightarrows Zn^{+2} + 2e^-$$

$$Cu \leftrightarrows Cu^{+2} + 2e^-$$

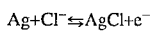

where the forward reaction is the oxidation reaction taking place at the anodic electrode and the reverse reaction is the reduction reaction taking place at the cathodic electrode. Other standard electrochemical reactions and their respective reduction potentials are well known in the art. See the *CRC Handbook of Chemistry and Physics*, pp D 151–58, 67th edition (1986–1987).

If the electrode assembly is to be used as an anode, the electrochemically reactive conductive filler preferably is a chemical species able to undergo oxidation during operation of the device. Suitable chemical species able to undergo oxidation include metals such as silver, zinc, copper, nickel, tin, lead, iron, chromium and other oxidizable species listed in the *CRC Handbook of Chemistry and Physics*, 57th edition, D-141 to D-146. Preferred chemical species able to undergo oxidation are metals, preferably in the form of powders. Most preferred are silver and zinc powders.

If the electrode assembly is to be used as a cathode, the electrochemically reactive conductive filler preferably is a chemical species able to undergo reduction during operation of the device. Suitable chemical species which are able to undergo reduction include silver chloride, silver bromide, silver hexacyanoferrate, and other reducible species listed in the *CRC Handbook of Chemistry and Physics*, 57th edition, D-141 to D-146. Of these, silver chloride is most preferred.

The donor and counter electrode assemblies each contain from about 1 to 50 vol % of an agent to be iontophoretically delivered through the body surface. Preferably, the polymeric matrix contains from about 10 to 50 vol % of the agent and most preferably from about 20 to 35 vol % of the agent. As used herein, the expression "agent" can mean a drug or other beneficial therapeutic agent when referring to the donor electrode assembly or an electrolyte salt when referring to the counter electrode assembly.

The electrode assemblies 8 and 9 can be formed by blending the desired agent (i.e., the drug or electrolyte), the conductive filler or fillers and other component(s), with the polymer by melt blending the conductive filler and agent into the polymer matrix and then casting the blend into a film using known solvent casting techniques, for example. On a Commercial scale however, the electrode assemblies 8 and 9 are preferably formed by pre-blending the conductive filler and agent into the polymer matrix in a mixer such as a Banbury mixer and then passing the pre-blended material through a rubber mill. Rubber milling involves repeatedly passing the materials through the nip of two rolls rotating at different speeds and in opposite directions. This method has been found to be particularly suitable when using a combination of carbon fibers and powdered metal as the conductive filler. In general, the material must be passed through multiple rubber mills, or alternatively, must be passed a number of times through a single rubber mill in order to achieve effective blending of the agent and conductive filler throughout the polymer matrix. Following the last rubber milling step, the material is preferably passed through one or more calendar rolls in order to obtain a precise film thickness.

Figure 4:
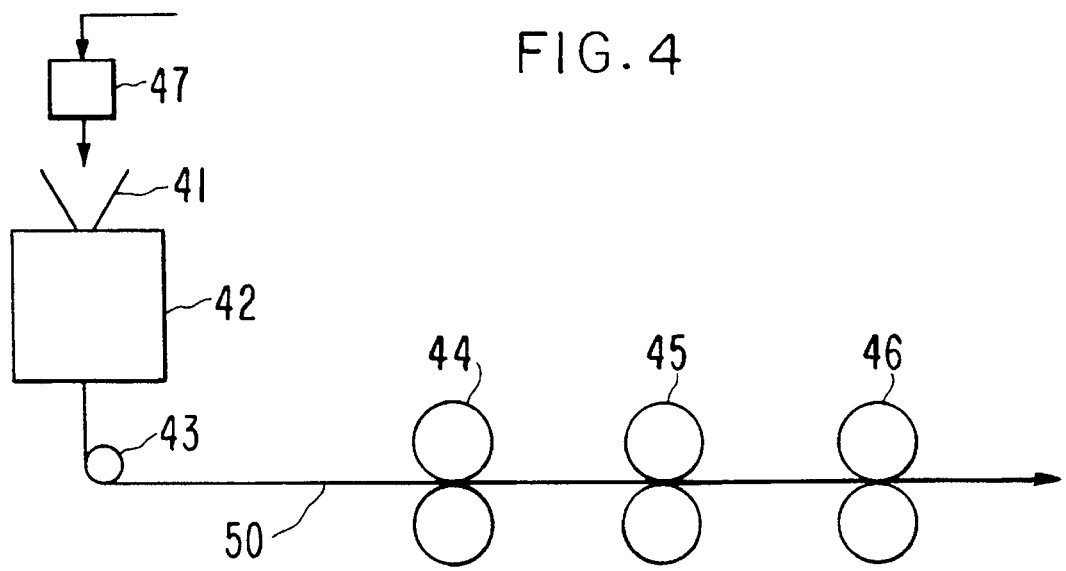
FIG. 4 is a schematic view of an apparatus used to make an electrode assembly according to the present invention.
Figure 5:
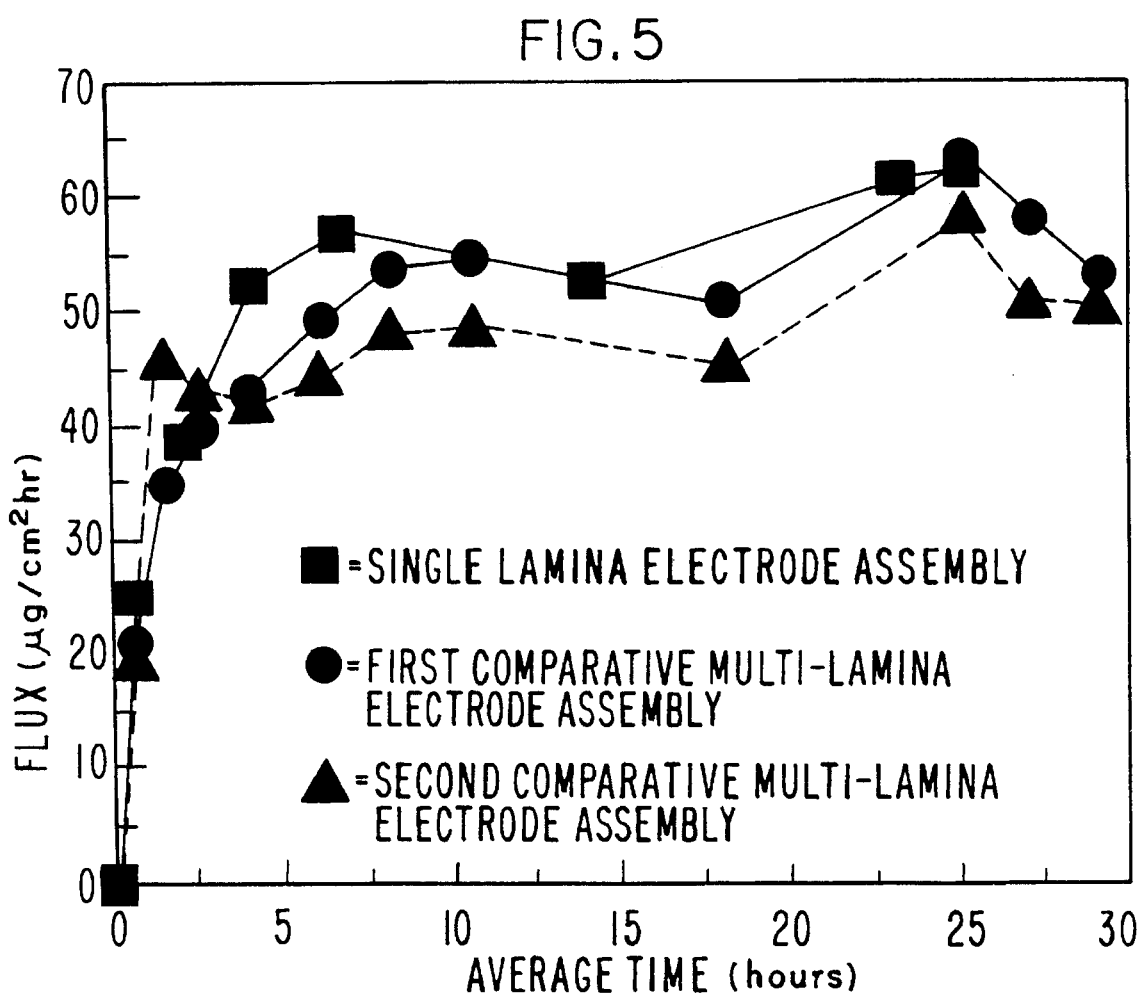
FIG. 5 is a graph of in vitro transdermal drug flux from an electrode assembly over time.

FIG. 4 is a schematic illustration of an apparatus used to manufacture the electrode assemblies of the present invention. The conductive filler, the agent and the polymer are first pre-blended in a suitable commercial mixer 47 such as a Banbury mixer or similar device. The pre-blended material is then fed into hopper 41 of mill 42. For example, the material fed into hopper 41 can be in the form of chunks of pre-blended polymer containing incompletely blended agent and filler therein. As mentioned above, mill 42 may contain one or more sets of opposed rollers rotating at different speeds and in different directions. In the case of a single mill (i.e., a single set of opposed rollers), the operator must recycle the milled material back through the rollers until the agent and the filler(s) are homogenously blended throughout the polymer matrix. In the case where mill 42 contains a plurality of sets of opposed rollers, the material can be successively milled on a continuous basis until the filler(s) and the agent are homogenously blended throughout the polymer matrix.

A sheet 50 of the blended material is formed after passing through the last pair of opposing rollers in the rubber mill 42. Sheet 50 passes over roller 43 and is fed into a series of calender rolls 44, 45, and 46. ! Calender rolls 44, 45, 46 are preferably heated. The temperature to which the calender rolls are heated will depend in large part on the specific polymer matrix used as well as the specific fillers blended therein. For example, when using an EVA 9 polymer matrix containing carbon fibers and/or silver powder, the calender rolls are typically heated to a temperature in the range of about 120° C. to 130° C. Another example is a polyisobutylene polymer matrix containing the same conductive fillers. The polyisobutylene film is typically heated to a temperature in the range of about 30° C. to 90° C. The calender rolls are preferably operated at a nip pressure of at least about 2000 psig. The final sheet 50 emerging from calender rolls 46 has an extremely uniform thickness, generally though not necessarily within the range of about 0.05 to 0.15 ±0.005 mm, with excellent blending of filler and agent throughout the polymer sheet.

Figure 2:
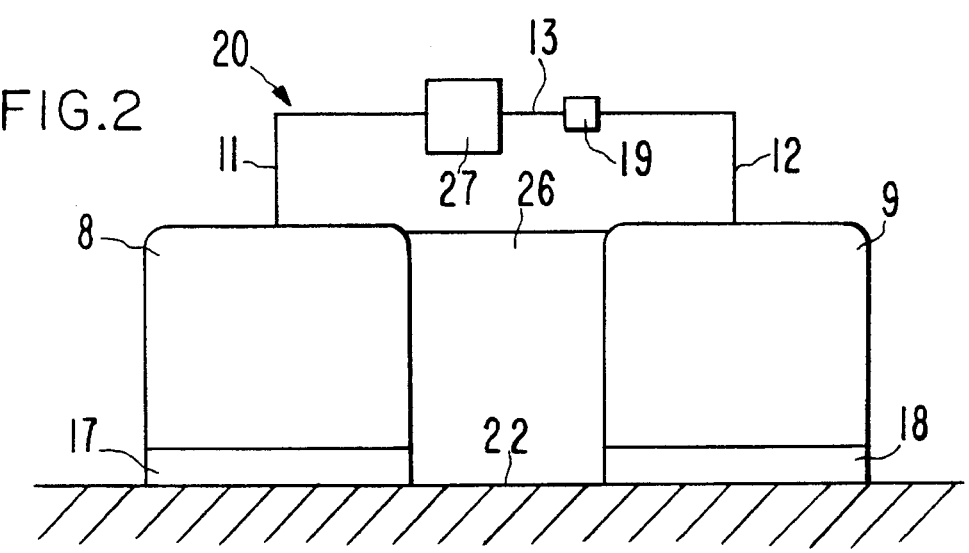
FIG. 2 is a schematic view of another embodiment of an iontophoretic delivery device according to the present invention.

FIG. 2 illustrates another iontophoretic delivery device designated by the numeral 20. Like device 10, device 20 also contains an electrical power source 27 (e.g., a battery) and an optional control circuit 19. However, in device 20 the donor electrode assembly 8 and the counter electrode assembly 9 are physically attached to insulator 26 and form a single self-contained unit. Insulator 26 prevents the electrode assemblies 8 and 9 from short circuiting by preventing electrical and/or ion transport between the electrode assemblies 8 and 9. Insulator 26 is preferably formed of a hydrophobic non-conducting polymeric material which is impermeable to both the passage of ions and water. A preferred insulating material is a nonporous ethylene vinyl acetate copolymer.

Alternatively, both the donor electrode assembly 8 and the counter electrode assembly 9 may be used to iontophoretically deliver different beneficial agents through body surface 22. For example, positive agent ions can be delivered through body surface 22 from the anodic electrode assembly, while negative agent ions can be delivered from the catholic electrode assembly. Alternatively, neutral drugs can be introduced from either electrode assembly by electroosmosis.

As an alternative to the side-by-side alignment of the donor electrode assembly 8, the insulator 26 and the counter electrode assembly 9 shown in FIG. 2, the electrode assemblies can be concentrically aligned with the counter electrode assembly positioned centrally and surrounded by the insulator 26 and the donor electrode assembly. The electrode assemblies can, if desired, be reversed with the counter electrode assembly surrounding the centrally positioned donor electrode assembly. The concentric alignment of the electrode assemblies can be circular, elliptical, rectangular or any of a variety of geometric configurations.

Figure 3:
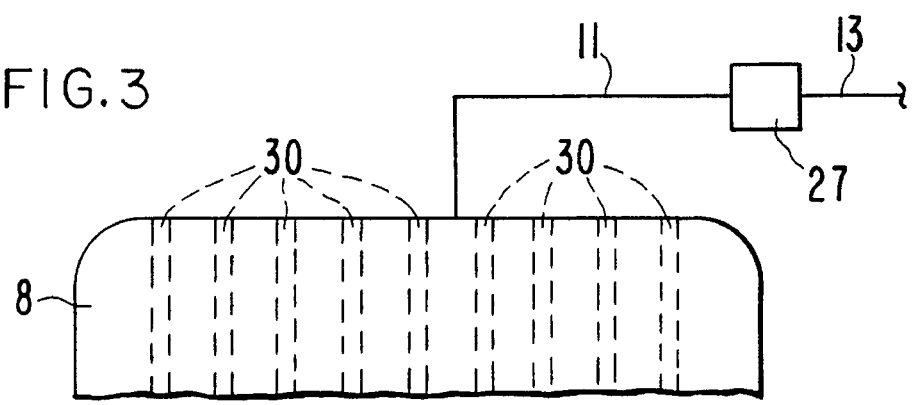
FIG. 3 is a side sectional view of another embodiment of an iontophoretic electrode assembly.

In one alternate embodiment shown in FIG. 3, electrode assembly 8 has a plurality of fluid flow pathways 30 running therethrough. Pathways 30 can be formed by any number of known means such as by punching the electrode assembly 8 after it is made or by forming the pathways at the time the electrode is made (e.g., by molding) using a mold insert. Alternatively, the pathways 30 in electrode assembly 8 (or electrode assembly 9) can be formed by mixing a sufficient quantity, generally about 10 to 50 vol %, preferably about 20 to 35 vol % and most preferably about 25 to 30 vol %, of a pore forming agent throughout the matrix of electrode assembly 8. In all of these cases, a plurality of pathways through the electrode assembly 8 are formed which can carry a solvent, such as water, therethrough. The electrode of FIG. 3 has an additional advantage in that it permits the delivery device, and specifically the electrode assemblies, to be manufactured in a non-hydrated condition, thereby giving the device a longer and more stable shelf life. Water, and/or another liquid solvent, can be applied to the electrode surface at the time of use. The pore forming agent sorbs solvent (e.g., water) thereby allowing water transport along a plurality of fluid flow pathways 30 through the "porous" electrode assembly matrix to hydrate electrode assembly(s) and place the device in an operational (i.e., hydrated) condition.

The pore-formers useful for forming the pathways 30 in electrode assemblies 8 and 9 include solids and pore-forming liquids. The expression pore-forming liquids generically embraces semi-solids and viscous fluids. The term pore-former for both solids and liquids includes substances that can be dissolved, extracted or leached from the electrode by a fluid, preferably water, to form an open-cell type porous structure. Additionally, the pore-formers suitable for the invention include pore-formers that can be dissolved, leached, or extracted without causing physical or chemical changes in the electrode polymer matrix. The pore-forming solids generally have a size of about 0.1 to 200 microns and they include alkali metal salts such as lithium carbonate, sodium chloride, sodium bromide, sodium carbonate, potassium chloride, potassium sulfate, potassium phosphate, sodium benzoate, sodium acetate, sodium citrate, potassium nitrite, and the like; the alkaline earth metal salts such as calcium phosphate, calcium nitrate, calcium chloride, and the like; the transition metal salts such as ferric chloride, ferrous sulfate, zinc sulfate, cupric chloride, manganese fluoride, manganese fluorosilicate, and the like; organic compounds such as polysaccharides including the sugars sucrose, glucose, fructose, mannitol, mannose, galactose, aldohexose, altrose, talose, sorbitol and the like. The pore formers can also be soluble polymers such as starch-graft poly(Na acrylate co-acrylamide) polymers, Carbowaxes®, CarboPol®, and the like. Preferred pore formers are starch-graft poly (Na-acrylate co-acrylamide) polymers sold under the trade name Waterlock® by Grain Processing Corp., Muscatine, Iowa. The pore-formers are non-toxic and form fluid flow pathways 30 through the electrode matrix. The pathways 30 are effective to convey water and/or other liquid solvent to the underlying drug or electrolyte reservoir, enabling the underlying reservoir to be quickly hydrated using an external source of liquid solvent (e.g., water) for quick start-up of the device.

Power source 27 is typically one or more batteries. As an alternative to a battery, device 10 can be powered by a galvanic couple formed by the current carrying member 11 and current carrying member 12 being composed of dissimilar electrochemical couples and being placed in electrical contact with one other. Typical materials for delivering a cationic agent into the body include a zinc donor current carrying member 11 and a silver/silver chloride current carrying member 12. A Zn-Ag/AgCl galvanic couple provides an electrical potential of about 1 volt.

Suitable polymers for use; as the matrix of electrode assemblies 8 and 9 include, without limitation, hydrophobic polymers such as polyethylene, polypropylene, polyisoprenes and polyalkenes, rubbers such as polyisobutylene, copolymers such as Kraton®, polyvinyl acetate, ethylene vinyl acetate copolymers, polyamides including nylons, polyurethanes, polyvinylchloride, cellulose acetate, cellulose acetate butyrate, ethylcellulose, cellulose acetate, and blends thereof; and hydrophilic polymers such as hydrogels, polyethylene oxides, Polyox®, Polyox® blended with polyacrylic acid or Carbopol®, cellulose derivatives such as hydroxypropyl methyl cellulose, hydroxyethyl cellulose, hydroxypropyl cellulose, pectin, starch, guar gum, locust bean gum, and the like, and blends thereof.

The adhesive properties of the electrode assemblies 8 and 9 may be enhanced by adding a resinous tackifier. This is especially important when using a non-tacky polymeric matrix. Examples of suitable tackifiers include products sold under the trademarks Staybelite Ester #5 and #10, Regal-Rez and Piccotac, all of Hercules, Inc. of Wilmington, Del. Additionally, the matrix may contain a theological agent suitable examples of which include mineral oil and silica.

The expressions "drug" and "therapeutic agent" are used interchangeably and are intended to have their broadest interpretation as any therapeutically active substance which is delivered to a living organism to produce a desired, usually beneficial, effect. In general this includes therapeutic agents in all of the major therapeutic areas including, but not limited to, anti-infectives such as antibiotics and antiviral agents, analgesics including fentanyl, sufentanil, buprenophine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine, ondansetron and granisetron, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers such as nifedipene, beta-blockers, beta-agonists such as dobutamine and ritodrine, antiarrythmics, antihypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, hypnotics, immunosuppressives, muscle relaxants, parasympatholytics, parasympathomimetrics, prostaglandins, proteins, peptides, psychostimulants, sedatives and tranquilizers.

The invention is also useful in the controlled delivery of peptides, polypeptides, proteins and other macromolecules. These macromolecular substances typically have a molecular weight of at least about 300 daltons, and mote typically a molecular weight in the range of about 300 to 40,000 daltons. Specific examples of peptides and proteins in this size range include, without limitation, LHRH, LHRH analogs Such as buserelin, gonadorelin, naphrelin and leuprolide, GHRH, insulin, insulotropin, heparin, calcitonin, octreotide, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteoids, αANF, growth factors such as growth factor releasing factor (GFRF), βMSH, somatostatin, bradykinin, somatotropin, platelet-derived growth factor, asparaginase, bleomycin sulfate; chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 antitrypsin (recombinant), TGF-beta. It is most preferable to use a water soluble salt of the drug or agent to be delivered.

The combined skin-contacting areas of electrode assemblies 8 and 9 can vary from less than 1 cm$^2$ to greater than 200 cm$^2$. The average device 10 however, will have electrode assemblies with a combined skin-contacting area within the range of about 5–50 cm$^2$.

As an alternative to the ion-conducting adhesive layers 17 and 18 shown in FIGS. 1 and 2, the iontophoretic delivery devices 10 and 20 may be self-adhering to the skin in cases where the polymer matrix is sufficiently tacky, either alone or by addition of suitable tackifying resins. Another alternative to, or to supplement the adhesiveness of, the ion-conducting adhesive layers 17 and 18 is an adhesive overlay. Any of the conventional adhesive overlays used to secure passive transdermal delivery devices to the skin may be used Another alternative/supplement to the ion-conducting adhesive layers 17 and 18 is a peripheral adhesive layer surrounding electrode assemblies 8 and/or 9 allowing electrode assemblies 8 and/or 9 to have a surface in direct contact with the patient's skin.

Having thus generally described our invention, the following examples will illustrate preferred embodiments thereof.

EXAMPLE I

An anodic electrode assembly was made by mixing powdered silver and graphite fibers into an ethylene vinyl acetate copolymer matrix. First, 21.4 g of ethylene vinyl acetate copolymer having a vinyl acetate content of 9% (EVA 9) were added to a 50 cm$^3$ Brabender mixer (Brabender Instruments, Inc., South Hackensack, N.J.). The mixer bowl was preheated to 90° C. and the blade speed was set at 20 rpm. The EVA 9 polymer was mixed for about five minutes until all of the pellets had been fused. Thereafter, 15.2 g of graphite fibers having a diameter of 8 microns and a length of 6.4 mm were slowly added into the mixer over a period of about five minutes. Thereafter, 70.9 g of silver powder having an average particle size of 4 microns was added to the mixer over a period of about five minutes. Thereafter, 9.0 g of metoclopramide monohydrochloride (catalog No. M0763, sold by Sigma Chemical Company of St. Louis, Mo.) were slowly added to the mixer over a period of about five minutes. Thereafter, the blade speed was increased to 40 rpm for an additional 20 minutes of mixing.

The blended material (about 180 cm$^3$) was then loaded into a melt press to produce a melt pressed film. The press had two platens which could be heated or cooled by circulating water/steam therethrough. The platens were heated to a temperature of 120° C. and the film was pressed at a pressure of 3000 psi. Periodically, the pressure was momentarily released in order to release air bubbles from the film. The melt pressed film was then passed between opposing calender rolls heated to about 95° C. The calendered film had a thickness of 6 mils.

Experiments were conducted to evaluate the drug delivery performance of the single lamina anodic film electrode assembly in comparison with the drug delivery performance of two different multi-lamina type electrode assemblies having separate and distinct electrode and drug reservoir layers. The apparatus used to measure the electrochemical performance of the electrodes included a two compartment diffusion cell having human cadaver skin clamped in the opening between the two compartments. A cathode containing silver chloride was mounted within the receptor compartment which was then filled with Dulbecco's phosphate buffered saline (pH 7). The single lamina anodic electrode assembly was attached to the skin sample on the donor side of the cell. The single lamina electrode assembly was fastened to the skin sample using an ion conducting adhesive composed of 80 vol % silicon adhesive and 20 vol % of a starch-graft poly (Na-acrylate co-acryl amide) polymer (Waterlock®, sold by Grain Processing Corp., Muscatine, Iowa). The flux of metoclopramide through the cadaver skin into the receptor solution was measured over a period of 25 hours using UV spectroscopy. The electrodes were connected in series with a potentiostat set to supply the necessary voltage to maintain a constant current level of 130 µA through the circuit. The skin contacting area was 1.3 cm$^2$ so the current density was 100 µA/cm$^2$.

A first comparative test used the same apparatus and test conditions described above except the single layer anodic electrode was replaced with a multi-lamina electrode assembly having an electrode layer comprised of an EVA 9 polymer matrix containing 25 vol % silver powder and 20 vol % carbon fibers. A second layer was comprised of a rayon polyester fabric. A third layer comprised of 40 vol % EVA 29, 25 vol % polyvinylpyrrolidone and 35 vol % metoclopramide HCl was the drug reservoir layer. The drug reservoir layer was adhered to the skin sample using the same ion conducting adhesive describe above.

A second comparative test used the same apparatus and test conditions described above except the anodic electrode was a multi-lamina electrode assembly having separate electrode and drug reservoir layers. The electrode layer was comprised of an EVA 9 polymer matrix loaded with 25 vol % silver powder and 20 vol % carbon fibers. The drug reservoir layer was comprised of a rayon polyester fabric soaked with a 0.1 wt % aqueous solution of metoclopramide HCl. The drug reservoir layer was adhered to the skin sample using the same ion Conducting adhesive described above.

The metoclopramide flux from both the single lamina and the multi-lamina electrode assemblies over time is shown in FIG. 4. As can be seen, the drug flux from the single lamina electrode assembly was at least as high it not higher than the drug flux from the multi-lamina electrode assemblies. Thus, the single lamina electrode assembly delivers drug as efficiently as the multi-lamina electrode assemblies but without the attendant risk of electrical failure between adjacent electrode assembly layers. Furthermore, because the electrode assembly is comprised of a single homogenous layer, the steps required to manufacture the electrode assembly are greatly simplified in comparison with the manufacture of a multi- lamina electrode assembly.

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. An electrically powered iontophoretic delivery device including a donor electrode assembly adapted to be placed in agent transmitting relation with a body surface, a counter electrode assembly adapted to be placed in agent transmitting relation with a body surface and a source of electrical power adapted to be electrically connected to the donor electrode assembly and the counter electrode assembly, wherein the donor electrode assembly comprises a polymeric matrix having a predetermined thickness, said matrix having homogeneously blended therein:

about 5 to 50 vol % of a conductive filler forming a conductive network through the entire thickness of the matrix; and about 1 to 50 vol % of a therapeutic agent to be iontophoretically delivered through the body surface in order to obtain a therapeutic effect.

2. The device of claim 1, wherein the polymeric matrix is selected from the group consisting of hydrophilic polymers, hydrophobic polymers and blends thereof.

3. The device of claim 2, wherein the polymeric matrix is comprised of a hydrophobic polymer selected from the group consisting of ethylene vinyl acetate copolymers, polyalkylenes, polyisoprenes, rubbers, polyisobutylene, polyvinylacetate, polyamides, polyurethanes, polyvinylchlorides, and modified cellulosic polymers.

4. The device of claim 2, wherein the polymeric matrix is comprised of a hydrophilic polymer selected from the group consisting of hydrogels, polyethylene oxides, cellulosic polymers, polyacrylic acids and polyvinyl pyrrolidones.

5. The device of claim 2, wherein the polymeric matrix comprises polyvinyl pyrrolidone.

6. The device of claim 1, wherein the polymeric matrix comprises an ethylene vinyl acetate copolymer.

7. The device of claim 1, containing about 15 to 30 vol. % of the conductive filler.

8. The device of claim 1, containing about 20 to 25 vol. % of the conductive filler.

9. The device of claim 1, wherein the conductive filler comprises an electrochemically reactive material able to undergo oxidation or reduction during operation of the device.

10. The device of claim 9, wherein the electrochemically reactive material is selected from the group consisting of Ag, Zn, Cu, silver halides, copper halides and $Ag_4Fe(CN)_6$.

11. The device of claim 1, wherein the conductive filler comprises an electrochemically inert material.

12. The device of claim 11, wherein the conductive filler is selected from the group consisting of carbon or graphite fibers, powdered carbon or graphite and electrochemically inert metals.

13. The device of claim 12, wherein the inert metal is selected from the group consisting of platinum, palladium, gold and stainless steel.

14. The device of claim 1, wherein a plurality of fluid flow pathways are provided through the electrode assembly.

15. The device of claim 14, wherein the fluid flow pathways are provided by a soluble pore forming agent in the polymeric matrix.

16. The device of claim 1, containing about 10 to 50 vol % of the therapeutic agent.

17. The device of claim 1, containing about 20 to 35 vol % of the therapeutic agent.

18. The device of claim 1, wherein the polymeric matrix comprised of about 10 to 60 wt % of a hydrophilic polymer and about 10 to 60 wt % of a hydrophobic polymer.

19. The device of claim 1, wherein the power source comprises a battery.

* * * * *